(12) United States Patent
Rohaninejad et al.

(10) Patent No.: US 10,492,812 B2
(45) Date of Patent: Dec. 3, 2019

(54) METHODS AND SYSTEMS FOR MAGNETICALLY SUSPENDING TISSUE STRUCTURES

(71) Applicant: Mohammadreza Rohaninejad, San Jose, CA (US)

(72) Inventors: Mohammadreza Rohaninejad, Saratoga, CA (US); Seyed Ali Mirnajafi, Irvine, CA (US); Mostafa Rohaninejad, Saratoga, CA (US); Morteza Rohaninejad, Saratoga, CA (US)

(*) Notice: Subject to any disclaimer, the term of this patent is extended or adjusted under 35 U.S.C. 154(b) by 0 days.

(21) Appl. No.: 15/824,101

(22) Filed: Nov. 28, 2017

(65) Prior Publication Data

US 2018/0078272 A1 Mar. 22, 2018

Related U.S. Application Data

(63) Continuation of application No. 15/384,098, filed on Dec. 19, 2016, now Pat. No. 9,855,068, which is a
(Continued)

(51) Int. Cl.
*A61B 17/29* (2006.01)
*A61B 17/28* (2006.01)
(Continued)

(52) U.S. Cl.
CPC ............ *A61B 17/29* (2013.01); *A61B 17/122* (2013.01); *A61B 17/1285* (2013.01);
(Continued)

(58) Field of Classification Search
CPC .... A61B 2017/2931; A61B 2017/2939; A61B 2017/294; A61B 2017/2946; A61B 17/29;
(Continued)

(56) References Cited

U.S. PATENT DOCUMENTS

| 1,472,992 A | 11/1923 | Roeglin |
| 7,169,104 B2 | 1/2007 | Ueda et al. |

(Continued)

FOREIGN PATENT DOCUMENTS

| WO | WO-2008089049 A1 | 7/2008 |
| WO | WO-2009019288 A2 | 2/2009 |

(Continued)

OTHER PUBLICATIONS

International search report dated Apr. 29, 2014 for PCT Application No. US2014/015807.
(Continued)

*Primary Examiner* — Samuel G Gilbert
(74) *Attorney, Agent, or Firm* — Wilson Sonsini Goodrich & Rosati

(57) ABSTRACT

A system for magnetically suspending tissue includes a grasper placement tool, a tissue grasper, a magnetic coupling element, and a tether which secures the magnetic coupling element to the tissue grasper. The grasper placement tool is used to simultaneously introduce both the tissue grasper and the magnetic coupling element to a body cavity. The grasper then releases the magnetic coupling element and engages a target tissue structure. The tissue grasper is then detached from the placement tool and a conventional laparoscopic or other grasper is used to engage the magnetic coupling element to an external magnet.

6 Claims, 15 Drawing Sheets

Related U.S. Application Data continuation of application No. 14/030,581, filed on Sep. 18, 2013, now Pat. No. 9,554,818.

(60) Provisional application No. 61/770,159, filed on Feb. 27, 2013.

(51) Int. Cl.
| | | |
|---|---|---|
| *A61B 17/122* | (2006.01) | |
| *A61B 17/128* | (2006.01) | |
| *A61B 34/00* | (2016.01) | |
| *A61B 17/00* | (2006.01) | |

(52) U.S. Cl.
CPC ........ *A61B 17/282* (2013.01); *A61B 17/2833* (2013.01); *A61B 34/73* (2016.02); *A61B 17/1227* (2013.01); *A61B 2017/00283* (2013.01); *A61B 2017/00473* (2013.01); *A61B 2017/00818* (2013.01); *A61B 2017/00876* (2013.01); *A61B 2017/2931* (2013.01); *A61B 2017/2946* (2013.01)

(58) Field of Classification Search
CPC . A61B 17/122; A61B 17/282; A61B 17/2833; A61B 17/0218; A61B 2019/2253; A61B 2019/2257
USPC ............ 600/37; 128/899; 606/139–143, 151, 606/157, 158, 205–211
See application file for complete search history.

(56) References Cited

U.S. PATENT DOCUMENTS

| | | | |
|---|---|---|---|
| 7,686,767 B2* | 3/2010 | Maschke | A61M 25/0127 600/435 |
| 7,766,810 B2 | 8/2010 | Ohdaira | |
| 8,529,435 B2* | 9/2013 | Linenkugel | A61B 1/00158 600/104 |
| 9,078,687 B2 | 7/2015 | Rohaninejad et al. | |
| 9,554,818 B2* | 1/2017 | Rohaninejad | A61B 17/282 |
| 9,855,068 B2 | 1/2018 | Rohaninejad et al. | |
| 2002/0107533 A1 | 8/2002 | Solingen | |
| 2007/0004958 A1 | 1/2007 | Ohdaira | |
| 2007/0135678 A1 | 6/2007 | Suzuki et al. | |
| 2007/0156028 A1 | 7/2007 | Van et al. | |
| 2007/0161855 A1 | 7/2007 | Mikkaichi et al. | |
| 2008/0171907 A1 | 7/2008 | Long et al. | |
| 2009/0043246 A1 | 2/2009 | Dominguez | |
| 2009/0192344 A1 | 7/2009 | Bakos et al. | |
| 2009/0306686 A1 | 12/2009 | Ohdaira | |
| 2010/0105984 A1 | 4/2010 | Brewer et al. | |
| 2010/0204727 A1* | 8/2010 | Dominguez | H01F 7/0252 606/205 |
| 2012/0088965 A1 | 4/2012 | Stokes et al. | |
| 2012/0238796 A1 | 9/2012 | Conlon | |

FOREIGN PATENT DOCUMENTS

| | | |
|---|---|---|
| WO | WO-2010041714 A1 | 4/2010 |
| WO | WO-2010121282 A1 | 10/2010 |
| WO | WO-2014133751 A1 | 9/2014 |

OTHER PUBLICATIONS

Notice of allowance dated Apr. 14, 2015 for U.S. Appl. No. 14/055,193.
Notice of Allowance dated Sep. 21, 2016 for U.S. Appl. No. 14/030,581.
Office Action dated Jan. 15, 2016 for U.S. Appl. No. 14/030,581.
Office action dated Apr. 1, 2014 for U.S. Appl. No. 14/055,193.
Office action dated Oct. 24, 2014 for U.S. Appl. No. 14/055,193.
U.S. Appl. No. 15/384,098 Notice of Allowance dated Aug. 31, 2017.
U.S. Appl. No. 15/384,098 Office Action dated Jun. 29, 2017.

* cited by examiner

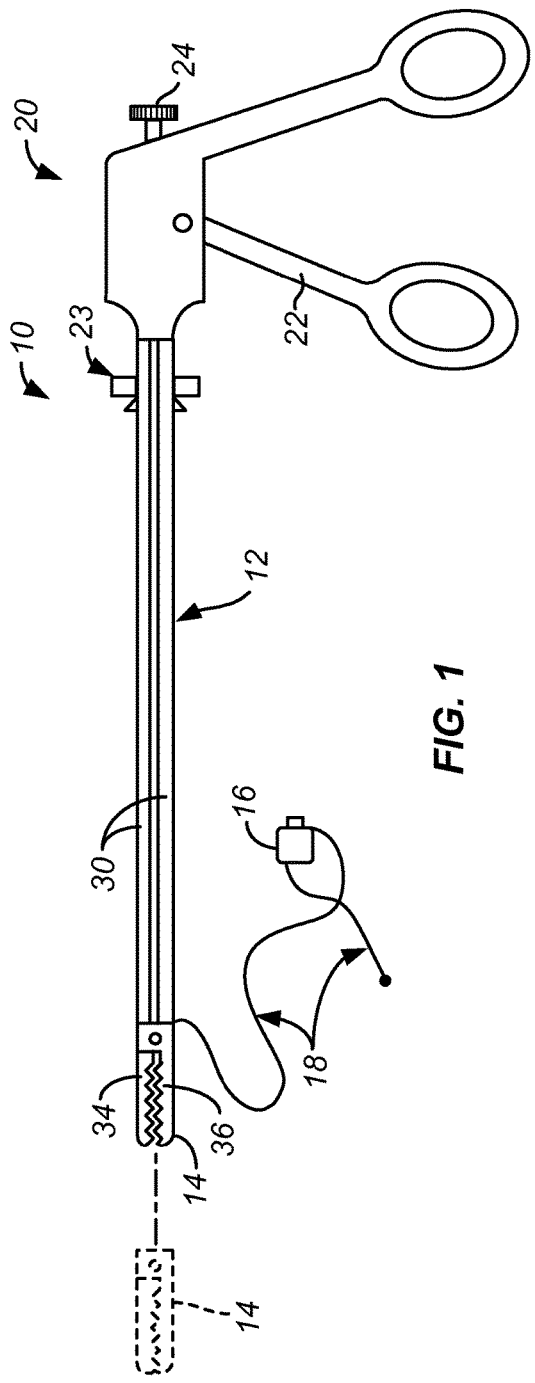
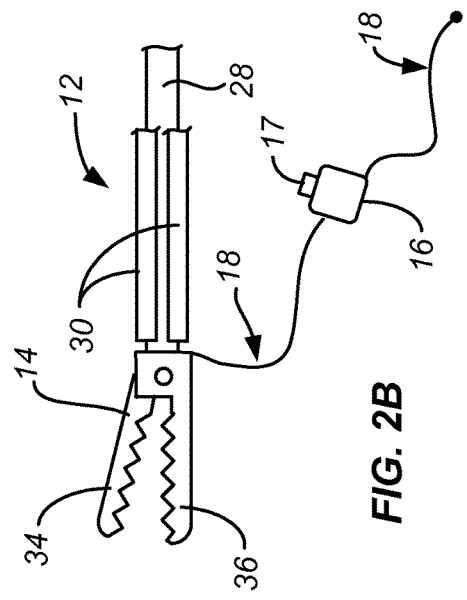
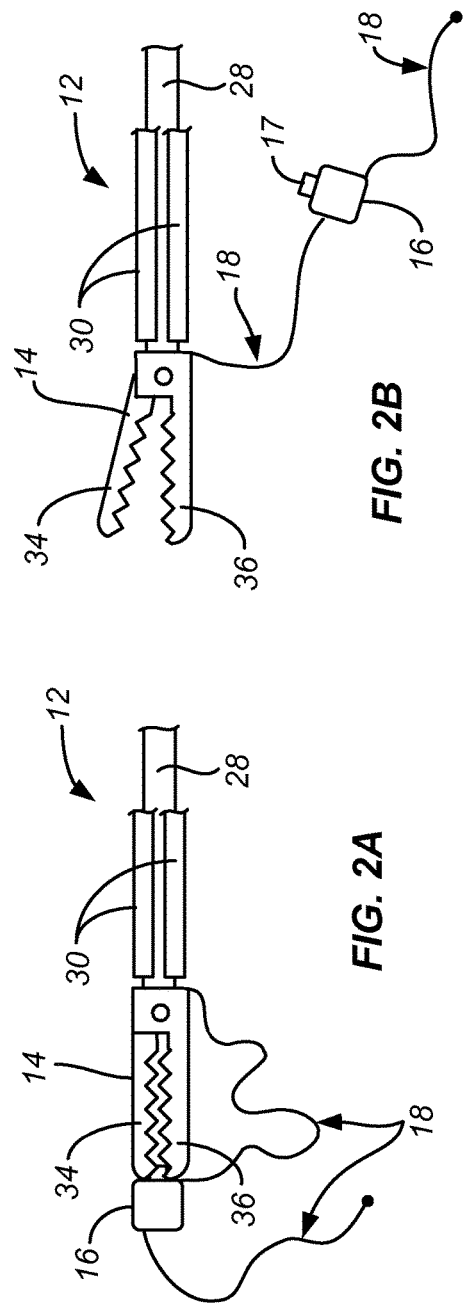
FIG. 1
FIG. 2A
FIG. 2B

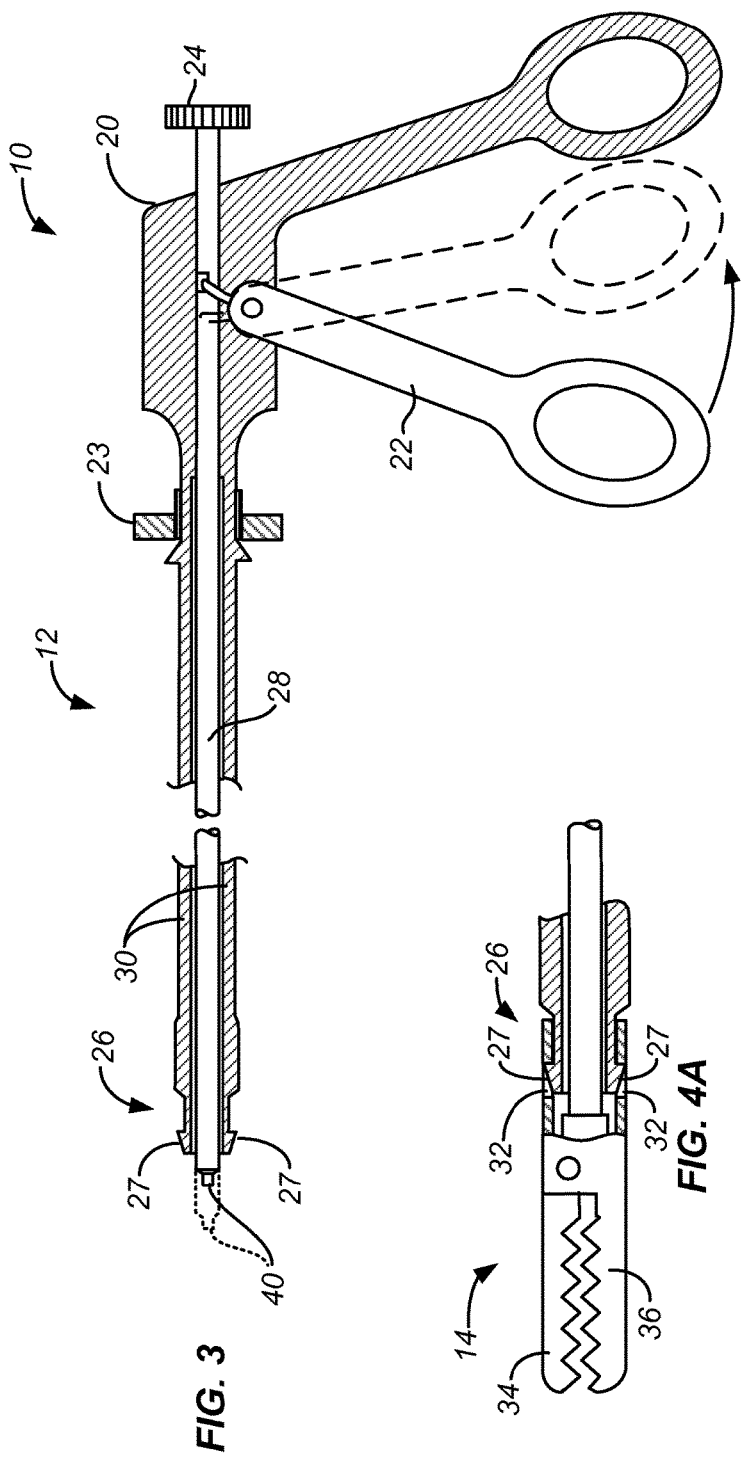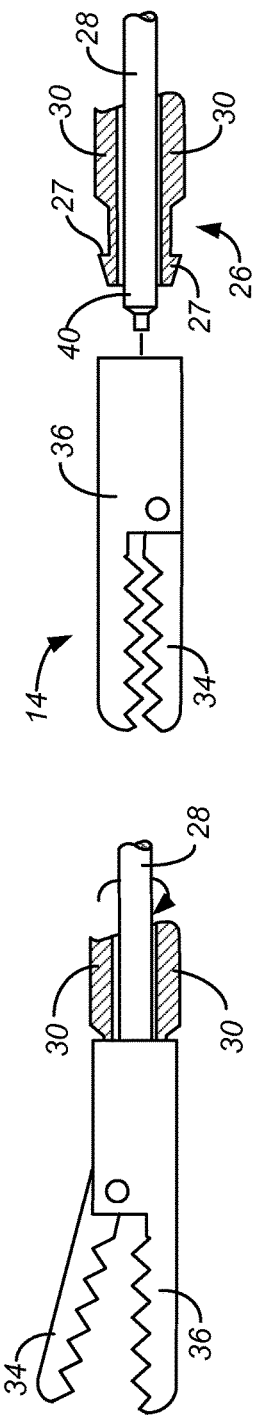

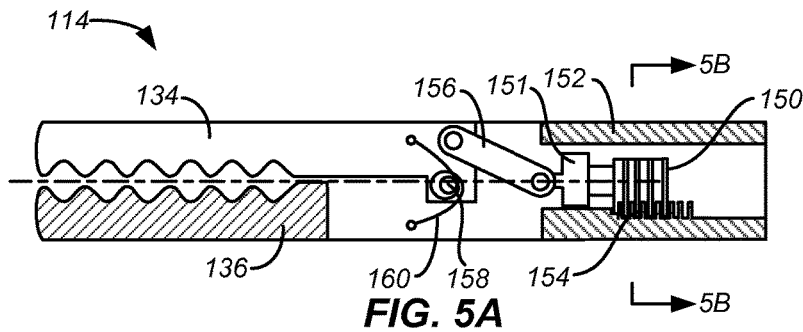
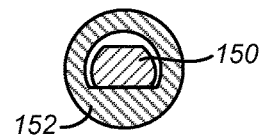
FIG. 5A  FIG. 5B
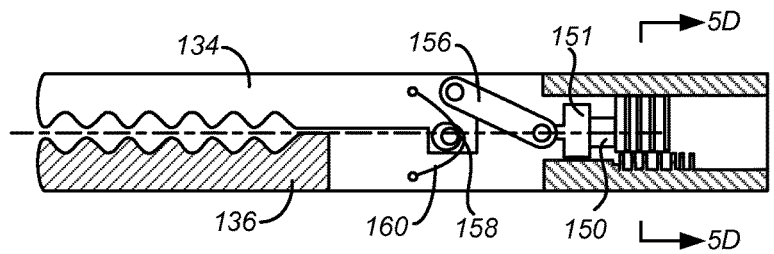
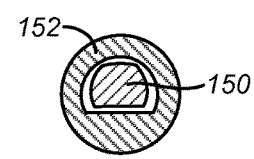
FIG. 5C  FIG. 5D
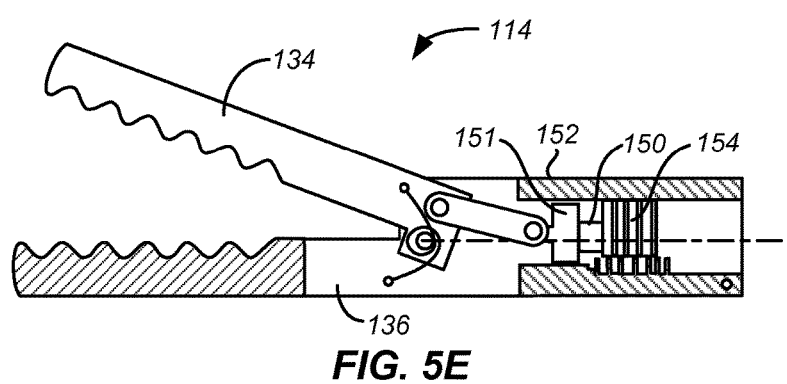
FIG. 5E
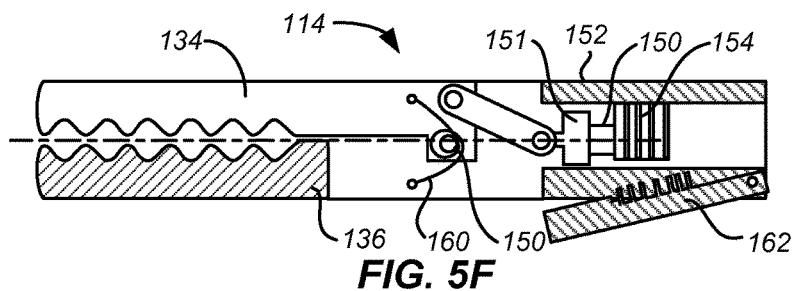
FIG. 5F

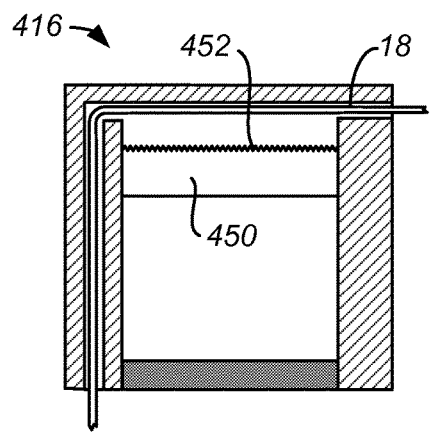
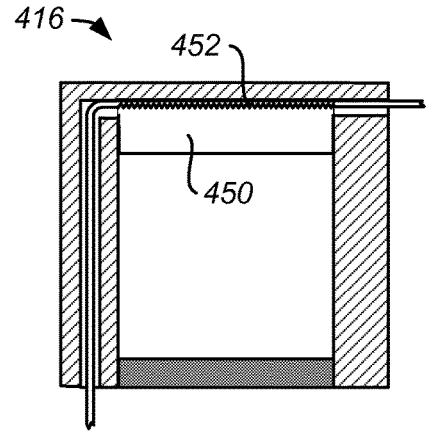
FIG. 8A  FIG. 8B
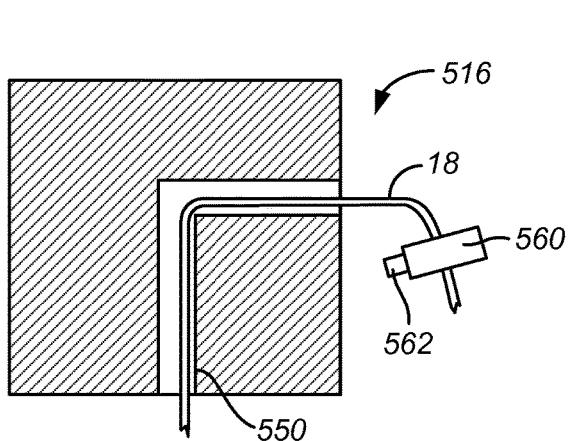
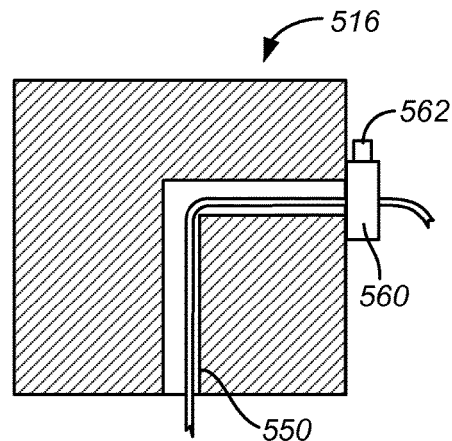
FIG. 9A  FIG. 9B

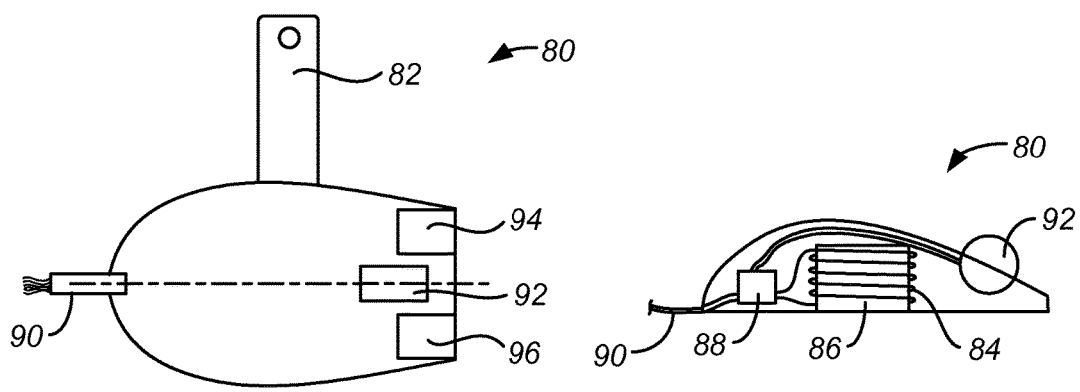
FIG. 12A    FIG. 12B
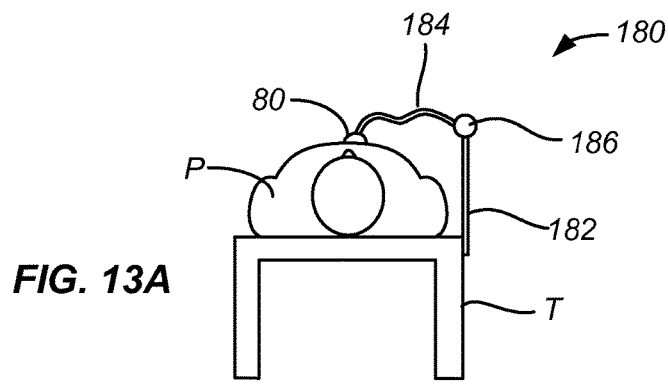
FIG. 13A
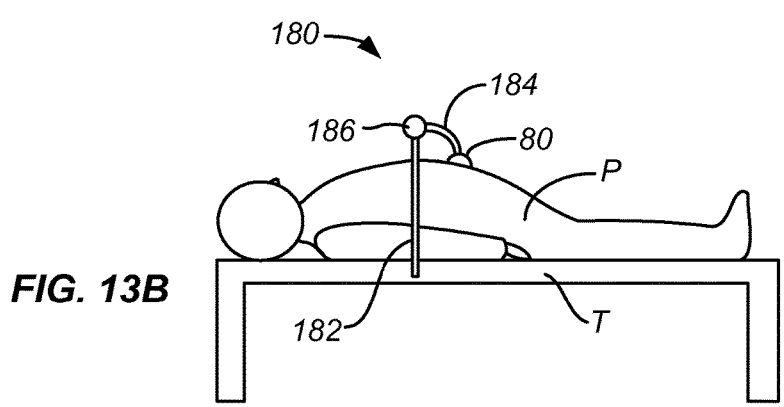
FIG. 13B

METHODS AND SYSTEMS FOR MAGNETICALLY SUSPENDING TISSUE STRUCTURES

CROSS-REFERENCE TO RELATED APPLICATIONS

This application is a continuation of U.S. patent application Ser. No. 15/384,098, filed Dec. 19, 2016, now U.S. Pat. No. 9,855,068, which is a continuation of U.S. patent application Ser. No. 14/030,581, filed Sep. 18, 2013, now U.S. Pat. No. 9,554,818, which claims the benefit of U.S. Provisional Application No. 61/770,159, filed on Feb. 27, 2013, the full disclosures of which are incorporated herein by reference.

BACKGROUND OF THE INVENTION

1. Field of the Invention

The present invention relates generally to medical devices and methods. More particularly, the present invention relates to methods and systems for magnetically suspending tissue structures during minimally invasive surgical procedures.

A number of surgical procedures which previously required open surgery are now performed by laparoscopy and other minimally invasive procedures. In laparoscopic procedures, a camera and a number of tools are introduced into a body cavity through ports or other passages formed through the patient's skin. In many procedures, the abdomen is insufflated and several ports are placed through the patient's abdominal wall. The camera is introduced through one of the ports, and the remaining ports are used for introducing tools needed to manipulate internal tissue structures and to remove, oblate, cauterize, cut, or otherwise modify these tissue structures.

One limitation of such laparoscopic and other minimally invasive procedures is the limited number of ports available at any one time to accommodate the tools required to perform the procedures. In order to reduce the number of needed ports, it has been proposed to use external magnets to suspend and position organs. The magnets could thus perform the role of a tissue grasper without the need to utilize one of the available access ports. For example, a magnetic element may be introduced into the body cavity through a port or otherwise. The magnetic element will be coupled to a target organ and an external magnet used to attract and position the magnetic element in order to in turn position the organ as needed for the procedure. Several specific systems for magnetically suspending organs and tissue structures are described in the references identified below in the Description of the Background Art.

Although quite promising, such magnetic tissue suspending systems have typically been cumbersome to deploy, difficult to reposition during a procedure, and difficult to release and remove after the procedure is over. It is an object of the present invention to overcome at least some of these deficiencies.

2. Description of the Background Art

U.S. Patent Publ. Nos. 2010/0204727; 2009/0043246; 20120088965; and 20120238796 and PCT Publication WO2009/019288 describe magnetic tissue suspension systems useful in laparoscopic procedures. U.S. Pat. No. 7,169,104 describes a magnetic tissue suspension system useful in endoscopic procedures. U.S. Pat. No. 7,766,810; U.S. Patent Publ. 2008/0171907; and WO2008/089049 describe systems for filling an organ with a magnetic material and thereafter magnetically manipulating the organ.

SUMMARY OF THE INVENTION

The present invention provides improved methods and systems for magnetically suspending and manipulating tissue structures during laparoscopy and other minimally invasive surgical procedures. The methods and systems provide a simplified and efficient protocol for introducing a tissue grasper attached to a magnetic element into a body cavity through a laparoscopic port or other tissue passage. The tissue grasper, magnetic element, and an adjustable tether connecting them together, are introduced simultaneously through the laparoscopic port or other tissue passage using a single shaft. After releasing the magnetic element from the shaft, the shaft is used to position the tissue grasper adjacent to the target tissue structure. The tissue grasper is then opened, placed over the tissue structure, and closed to firmly grasp the tissue structure. The tissue grasper is then released from the single shaft and the shaft removed from the body cavity. A conventional or other laparoscopic grasper is then introduced into the body cavity to grasp the magnetic element and position the magnetic element adjacent to an external magnet which attracts the magnetic element and allows positioning the element by moving the external magnet over the patient's skin. The laparoscopic grasper can also be used to tighten or cinch the tether by pulling on the tether which locks in place after appropriate tensioning.

A particular object of the present invention is to provide variable control of the magnetic field which is created between the magnetic coupling element within the body cavity and the external suspension magnet present over the patient's skin. While the use of fixed magnets and/or magnetic materials which are not themselves magnets comes within the scope of the present invention, it will be preferable if at least one of the magnetic coupling element and the external suspension magnet is configured to provide an adjustable magnetic field. The most common magnets having adjustable field strength are electromagnets, which typically comprise a wound helical coil of wire, usually having an iron core. When current flows through the helical coil, the iron core acts as a magnet, where the strength and polarity of the magnetic field created are adjustable by changing the magnitude of and/or the direction of current flow through the wire. A variety of conventional circuits are available for coupling to an electromagnet to provide a variable, adjustable magnetic field.

While usually at least one of the magnetic coupling element and the external suspension magnet will have an adjustable magnetic field, the other magnetic element may be a permanent magnet or a temporary magnet. Permanent magnets are those which retain a generally fixed level of magnetism over time and which are typically made of permanently magnetizable materials, such as neodymium-iron-boron alloys, samarium-cobalt alloys, alnico alloys, as well as ceramic and ferrite materials. Temporary magnets are typically made from iron and other ferrite materials.

While using an electromagnet or other magnet having an adjustable field as the external suspension magnet will be most common, it will also be possible to use an electromagnet or other adjustable field magnet as the magnetic coupling element within the body cavity. In some cases, it will be desirable to form both the external suspension magnet and the magnetic coupling element as electromagnets or other adjustable field strength magnets. It will be appreciated that by having both the external suspension magnet and the internal magnetic coupling element be capable of providing an adjustable magnetic field, the magnetic traction between these magnetic elements can be adjustable over a wide range of field strengths. The ability to adjust the field strength is desirable for many reasons. For example, the strength may be adjusted when it is desirable to move the external suspension magnet over the patient's body surface in order to pull or drag the internally located magnetic coupling element. It will also be desirable to be able to adjust the magnetic field strength at different portions of the surgical procedure. A strong magnetic field may be necessary at times that significant tension is being placed on the tether. At other times, however, it may be desirable to reduce the magnetic strength between the magnetic coupling element and the external suspension magnet, for example in order to lessen the compressive force being applied to the tissue in order to reduce the inhibition of blood circulation over extended time periods. The electromagnet will usually include a controller unit, and the controller unit will usually be adjustable or programmable for one or more purposes. For example, software may be provided to determine or calculate the optimal magnetic force to accommodate an abdominal thickness, tool size, supporting force, or the like, and to calculate the desired holding force and the electrical power needed to generate the desired force.

In a first aspect of the present invention, a tissue suspension system comprises a grasper placement tool having a shaft, a tissue grasper, a magnetic coupling element, and a tether securing the magnetic coupling element to the tissue grasper. The tissue grasper is detachably secured to a distal end of the shaft, allowing the tissue grasper to be released once it has been secured to a target tissue structure. Such a release mechanism eliminates the need to provide a separate tool to remove and place the tissue grasper as required by several of the proposed system.

In a preferred aspect, the grasper placement tool has a rigid narrow shaft configured for laparoscopic introduction into a patient's insufflated abdomen. Typically, the shaft will have a diameter intended for insertion through a convention laparoscopic port, e.g. having a diameter of 5 mm, 10 mm, or 12 mm. The tissue grasper may be secured to the shaft of the grasper placement tool by any suitable mechanical attachment mechanism, typically being a bayonet attachment which can be released via a mechanism located at a proximal end of the shaft. The tissue grasper typically includes a pair of clamping jaws which can be opened and closed from the proximal end of the shaft. The tissue grasper is specifically configured to be closed over the tissue structure while the tissue grasper remains attached to the shaft. The tissue grasper is further preferably configured to remain closed over the tissue even after being detached from the shaft.

In specific embodiments of the present invention, the jaws of the tissue grasper will be attached to a rod which can be moved in order to open and close the jaws. Typically, the tissue grasper placement tool includes a driver which engages the rod of the tissue grasper allowing the rod to be reciprocated in order to open and close the jaws while the tissue grasper remains on the shaft.

In further specific embodiments, the magnetic coupling element will be configured so that it can be carried by the jaws when the grasper placement tool is being introduced into the body cavity. In such configuration, the magnetic element, the tissue grasper, and the shaft of the tissue grasper placement tool will preferably be coaxially aligned in order to minimize the profile and allow the assembly to be introduced through a laparoscopic or other port simultaneously in a single motion. That is, the tissue grasper will have an axis which is aligned with an axis of the shaft and usually with an axis of the magnetic element. This allows the shaft, tissue grasper, and magnetic element to be inserted together in tandem through the laparoscopic port of other access passage.

The length of tether between the tissue grasper and the magnetic element is preferably adjustable. For example, the tether may be configured to be pulled through the magnetic coupling element and to be selectively locked once a proper tension on the tissue structure has been achieved. A variety of suitable locking mechanisms may be provided on the magnetic element, including mechanically actuable locking mechanisms and magnetically actuable locking mechanisms. In some embodiments, as a safety measure, the locking mechanism can be configured to allow the tether to slip when excessive tension is applied.

The assembly of the tissue grasper placement tool, magnetic element, and tether, as just described, will usually be combined in a system that further includes the external magnet and optionally a frame, arm or other support structure for holding the external magnet in place during a procedure. Such support structures will typically be configured to be secured to a table and they may optionally include a shape lock mechanism for facilitating repositioning.

In a second aspect, the present invention comprises a method for supporting an internal tissue structure using an external magnet. A shaft is introduced through a percutaneous passage, such as a laparoscopic port, into a body cavity of a patient, such as an insufflated abdomen. A distal end of the shaft carries a tissue grasper and a magnetic coupling element. The tissue grasper is secured to the magnetic coupling element by a tether. The magnetic coupling element is released from the shaft within the cavity while maintaining connected to the grasper by the tether. The tissue grasper is then secured over the tissue structure while the grasper remains on the shaft. Usually, a driver or other mechanism in the shaft is used to lock the grasper in the required gripped position. The tissue grasper is then released from the shaft after having been secured over the tissue structure. The external magnet is then positioned over the patient's skin to attract and hold the magnetic coupling element in place. The tether is then cinched to position the tissue structure as desired.

The shaft, tissue grasper, and magnetic coupling element are usually aligned in tandem as they are introduced through the percutaneous passage. Such an aligned configuration simplifies the introduction of these three system components, significantly reducing the complexity of the procedure. Typically, the magnetic coupling element is carried by the tissue grasper while being introduced through the port of other tissue passage, and the magnetic coupling element can be released by simply opening the tissue grasper.

The tissue grasper typically comprises opposed jaws, and securing the tissue grasper over the tissue comprises closing the jaws over the tissue where the jaws remain closed after the tissue grasper has been released from the shaft. In specific embodiments, closing the jaws over the tissue structure comprises actuating a driver in the shaft to cause the jaws to close where the jaws remain closed after such actuation stops.

Releasing the tissue grasper from the shaft typically comprises actuating a coupling mechanism, such as a bayonet connector, on the shaft, to release the tissue grasper. The methods may further comprise positioning the external magnet using a supporting structure, such as support arm attached to the patient bed or operating table. Cinching the tether may comprise grasping the tether and pulling the tether through a lock on at least one of the magnetic coupling element in the tissue grasper. The methods may further comprise releasing the tissue grasper from the tissue structure after the procedure has been completed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the grasper placement tool connected to a tissue grasper and a magnetic element in accordance with the principles of the present invention.

FIGS. 2A and 2B are detailed end views of the grasper placement tool of FIG. 1 shown with the tissue grasper holding the magnetic element (FIG. 2A) and with the tissue grasper open (FIG. 2B).

FIG. 3 is a cross-sectional view of the grasper placement tool of FIG. 1 shown without the tissue grasper.

FIG. 4A is a detailed, end view of the grasper placement tool shown with a bayonet connector holding the tissue grasper in place.

FIG. 4B is a detailed, end view of the grasper placement tool shown with the jaws of the tissue grasper open.

FIG. 4C is a detailed, end view of the grasper placement tool of the present invention shown with the tissue grasper detached from the bayonet connector.

FIGS. 5A-5F illustrate a first exemplary embodiment of a tissue grasper constructed in accordance with the principles of the present invention.

FIGS. 8A and 8B illustrate a first embodiment of an exemplary magnetic element constructed in accordance with the principles of the present invention.

FIGS. 9A and 9B illustrate a second exemplary embodiment of a magnetic element constructed in accordance with the principles of the present invention.

FIGS. 12A and 12B illustrate an exemplary external magnet constructed in accordance with the principles of the present invention.

FIGS. 13A and 13B illustrate the external magnet being supported by a shape-lock arm in accordance with the principles of the present invention.

DETAILED DESCRIPTION OF THE INVENTION

Figure 5G:
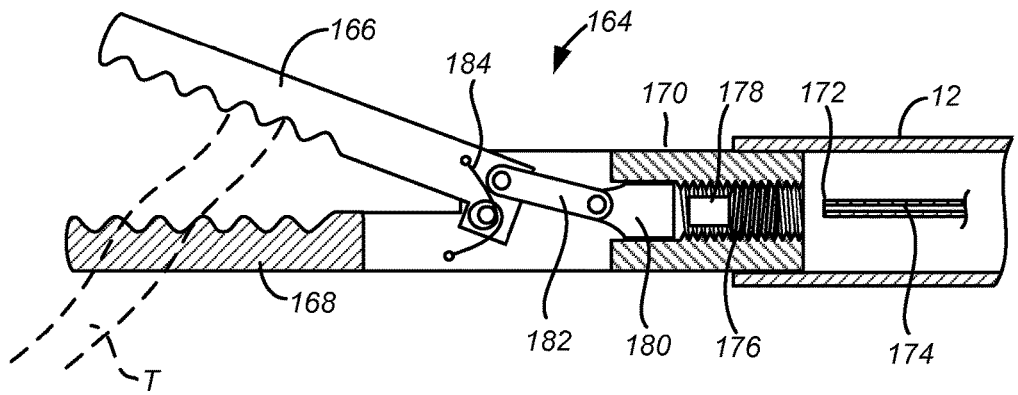
FIGS. 5G-5I illustrate a second exemplary embodiment of a tissue grasper constructed in accordance with the principles of the present invention.

Referring to FIG. 1, a tissue grasper placement tool 10 includes a shaft 12 which carries a tissue grasper 14 at its distal end. A magnetic element 16 is secured to the tissue grasper 14 by a tether 18. A handle 20 at the proximal end of shaft 12 includes a trigger 22 which is used for opening and closing the oppose jaws 34 and 36 and also for detaching the tissue grasper 14 from the shaft 12, as will be described in more detail below. A detachment sleeve 23 on shaft 12 is also provided to detach the tissue grasper 14, and a rotatable knob 24 is provided at the proximal end of a driver 28 (FIGS. 2A, 2B and 3) and is used to lock the opposed jaws 34 and 36 of the tissue grasper 14 in place in any desired position, as will also be described in more detail below.

Referring now to FIGS. 2A and 2B, the tissue grasper 14 will preferably hold the magnetic element 16 between the opposed jaws 34 and 36, as shown in FIG. 2A, while the tool end is being introduced into a target body cavity through a laparoscopic port or other tissue passage. Once in place, the jaws 34 and 36 may opened, as shown in FIG. 2B, to release the magnetic element 16. In the open configuration of FIG. 2B, the jaws 34 and 36 of tissue grasper 14 will also be in position to engage and be tightened over a target tissue structure, as will be described in more detail below.

Referring now to FIG. 3, a bayonet connector 26 used for detachably securing the tissue grasper 14 in the position shown in FIG. 1. The bayonet connector may be of generally conventional construction, including one or a pair of detents 27 which are received in opposed apertures 32 (FIG. 4A) in a shank region of the tissue grasper 14. The shaft 12 is axially split into a pair of opposed prongs 30 which may be squeezed together in order to release the detent pins 27 when it is desired to detach the tissue grasper 14 from the shaft. The grasper release mechanism 23 allows the user to close the prongs and the trigger 22 can be used to advance the driver 28 to push the grasper off of the bayonet connector. As shown in FIG. 3, the trigger 22 may be pulled (as shown in broken line) to advance a distal end 40 of the driver 28 (as also shown in broken line).

Referring now to FIG. 4B, the rotatable knob 24 may be used to rotate driver 28 (as shown by an arrow) in order to lock the opposed jaws 34 and 36, as will be described in greater detail below.

FIG. 4C illustrates the tissue grasper 14 after the jaws have been closed and the grasper released from the bayonet connector 26.

Referring now to FIGS. 5A-5F, a first exemplary tissue grasper 114 will be described. The tissue grasper 114 comprises an upper jaw 134 pivotally attached to a lower jaw 136 and having a shank region 152 at a proximal end thereof. Although not illustrated in FIGS. 5A-5F, the bayonet connector 26 of the shaft 30 of the grasper placement tool 10 will be received within the open end of the shank and will engage apertures (as described previously for detachably securing the tissue grasper 114). The distal end 40 of the driver 28 will be configured to engage a proximal end (to the right in FIG. 5A) of a piston 150 with a threaded proximal end 154. The threaded end 154 is rotatably attached to a follower 151 secured to a link 156. In this way, the driver 28 can be used to rotate the piston between a locked configuration, as shown in FIG. 5A, where the threads on the piston engage mating threads on an inner surface of the shank 152, and an unlocked configuration as shown in FIG. 5C, where the piston has been rotated 180 degrees so that the threads no longer engage each other. In the unlocked configuration of FIGS. 5C and 5D, the driver 28 may be used to advance the piston distally to close the upper jaw 134, as shown in FIG. 5E. The piston 150 may then be rotated back to the position of FIG. 5A and FIG. 5B in order to lock the jaw closed if desired. Otherwise, a spring 160 may be configured to self-open the jaws when the piston is free to translate and no force is applied to piston by the driver 28. Optionally, a portion 162 of the shank 152 may be pivotally attached so that the portion may be opened to disengage the piston whenever desired, allowing the jaws to open.

In variations of the grasper 114 of FIGS. 5A-5F, the shank 152 may be replaced by a cylinder with a full internal thread. The follower 151 and the threaded end 154 of the piston 150 remain rotatably coupled, and a hex or other driver can be temporarily engaged with the shank 152 and piston 150 to rotate the threaded end 154 to translate the piston distally and proximally within the shank to open and close the jaws 134 and 136. When the piston 150 is fully distally advanced against the follower, the jaws will remain locked until the driver is re-engaged to drive the piston 150 proximally to release the jaws.

Figure 5H:
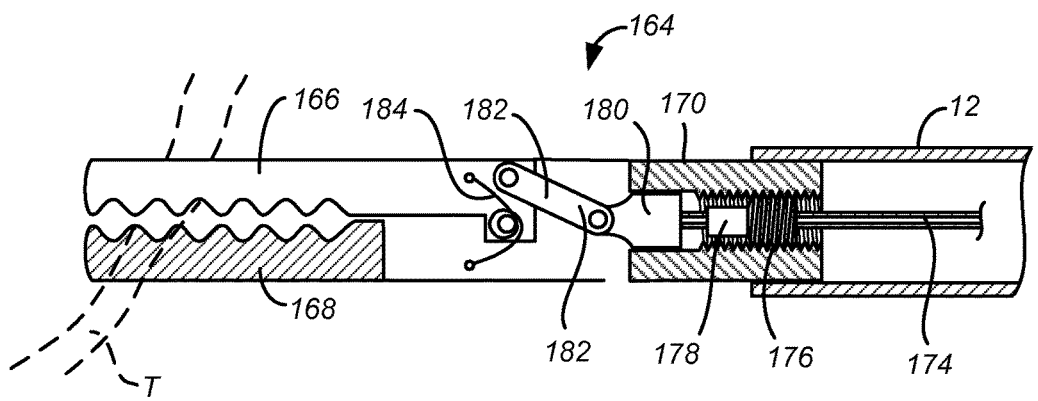
Figure 5I:
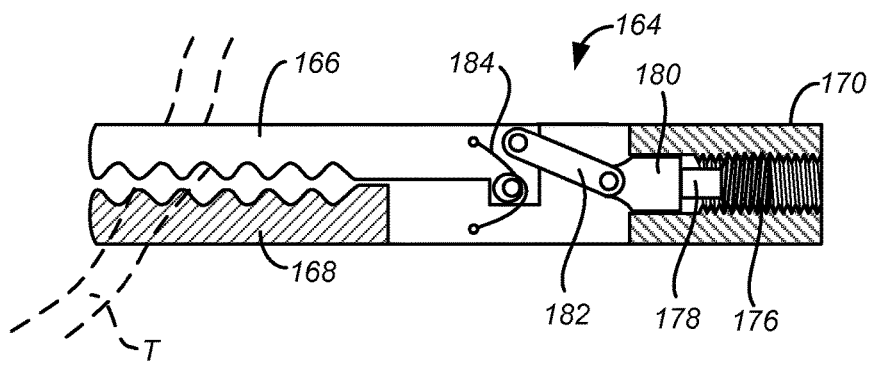

Referring now to FIGS. 5G-5I, a second exemplary tissue grasper 164 will be described. The tissue grasper 164 comprises an upper jaw 166 pivotally attached to a lower jaw 168 and having a shank region 170 at a proximal end thereof. The shank region 170 is detachably received in an open end of the shaft 12 of the previously illustrated tissue grasper placement tool 10. A distal end 172 of a hex driver shaft 174 is configured to pass through a complementary hexagonal axial passage through a threaded piston 176 having a protruding distal end 178. A follower 180 is pivotally attached to one end of a link 182 which is pivotally attached at its other end to the upper jaw 166. In this way, the hex driver 174 can be passed through the passage in the follower 180 to engage a proximal end of the follower to close the upper jaw 166 as shown in FIG. 5H. Once the jaws have been closed over a target tissue T, the hex driver 174 can be rotated to drive the threaded piston 176 forward to lock the jaws over the tissue. As with earlier embodiments, a spring 184 is provided to hold the jaws 166 and 168 open, as shown in FIG. 5G, when the follower 180 is proximally retracted. When it is desired to release the jaws, the hex driver 174 and shaft 12 may be re-engaged with the shank 170 and the hex driver used to rotate the threaded piston 176 to release the force against the follower 174, allowing the spring 184 to open the jaws.

Figure 6A:
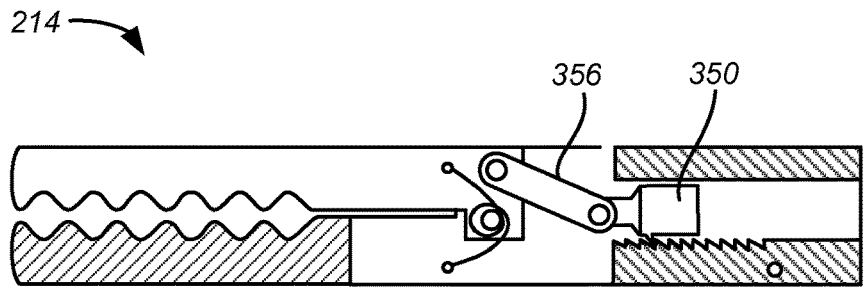
FIGS. 6A and 6B illustrate a third exemplary embodiment of a tissue grasper constructed in accordance with the principles of the present invention.
Figure 6B:
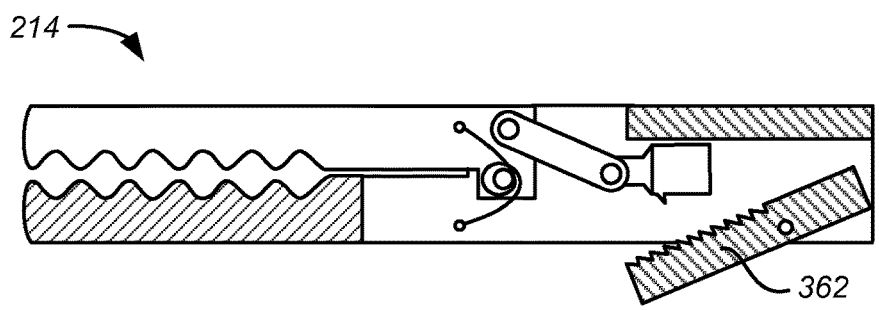

Referring now to FIGS. 6A and 6B, an alternative tissue grasper 214 is illustrated. A piston 350 is attached through a link 356, and the opening/closing mechanism is similar to that described relative to FIGS. 5A-5F. The piston 350, however, is not rotatable and the only means for locking and unlocking the axial translation of the piston is a pivoting wall 362. Thus, the piston 350 is locked as shown in FIG. 6A and is unlocked as shown in FIG. 6B.

Figure 7A:
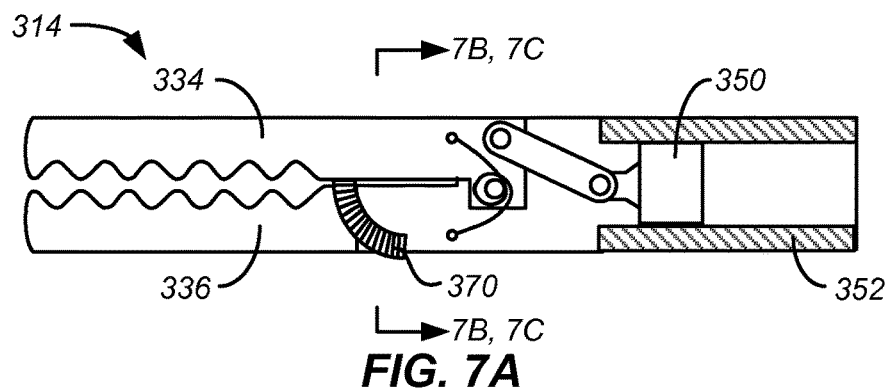
FIGS. 7A-7C illustrate a fourth embodiment of a tissue grasper constructed in accordance with the principles of the present invention.
Figure 7B:
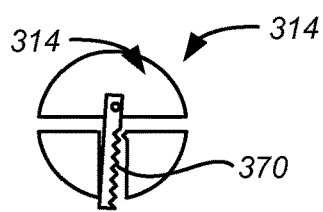
Figure 7C:
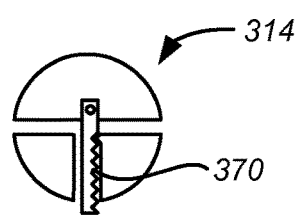

A second alternatively designed tissue grasper 314 is illustrated in FIGS. 7A-7C. Piston 350 is free to axially translate in either a proximal or distal direction within shank 352. The upper jaw 334 is locked relative to the lower jaw 336 by a curved ratchet strip 370 which can be opened as shown in FIG. 7B or closed as shown in FIG. 7C in order to permit or prevent opening and closing of the jaws.

Referring now to FIGS. 8A and 8B, a first exemplary embodiment of a magnetic coupling element 416 is illustrated. The tether 18 passes at a 90 degree angle from one corner of the magnetic element to an opposed corner. A magnetic shuttle 450 can be moved from an open configuration, as shown in FIG. 8A, where the tether 18 is free to move through the magnetic element 416 to a closed configuration, as shown in FIG. 8B, where the tether 18 is locked relative to the magnetic element. The magnetic shuttle 450 may be actuated, for example, when the magnetic element 416 is being held by the external magnet which will draw the magnetic shuttle 450 into the locked configuration as shown in FIG. 8B. This configuration is particularly convenient since no separate action is needed to lock and unlock the tether. By properly orienting surface features 452, the tether 18 may be drawn in a cinching or tightening direction even when the shuttle is closed, but prevented from moving in the opposite direction since the features 452 will cut or bite into the tether if it moves in the opposite direction.

Referring now to FIGS. 9A and 9B, an alternative magnetic element 516 is illustrated where tether 18 passes through an open passage 550. Once the tether is sufficiently tight, a locking element 560 can be moved against the body of the magnetic element 516, shown in FIG. 9B in order to prevent the tether 18 from being pulled out of the passage 550. The locking element 560 can be a conventional spring lock with a button 562 available to release the lock.

Figure 10A:
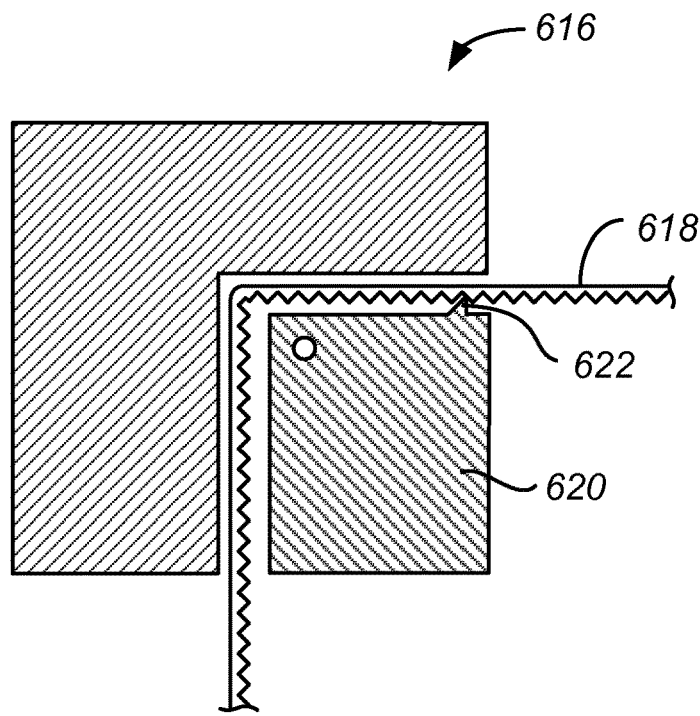
FIGS. 10A and 10B illustrate a third exemplary embodiment of a magnetic element constructed in accordance with the principles of the present invention.
Figure 10B:
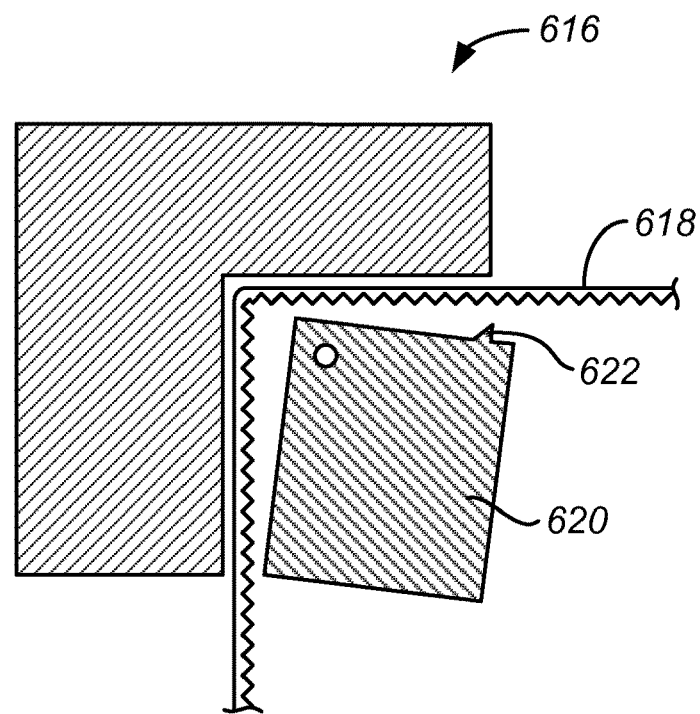

Referring now to FIGS. 10A and 10B, a second alternative magnetic element 616 is illustrated. The tether has a ratcheted section 618 which travels past a pivoted element 620. The pivotable element 620 carries a tooth 622 which engages the ratchets 618 to prevent the tether from being drawn out of the magnetic element. The tether, however, may be tightened as the ratchet will travel over the tooth 622 in that direction only. A torsion or other spring element (not illustrated) is usually provided to urge the pivotable element 620 in a clockwise rotational direction against the ratcheted section 618 of the tether, as viewed in FIGS. 10A and 10B.

Figure 10C:
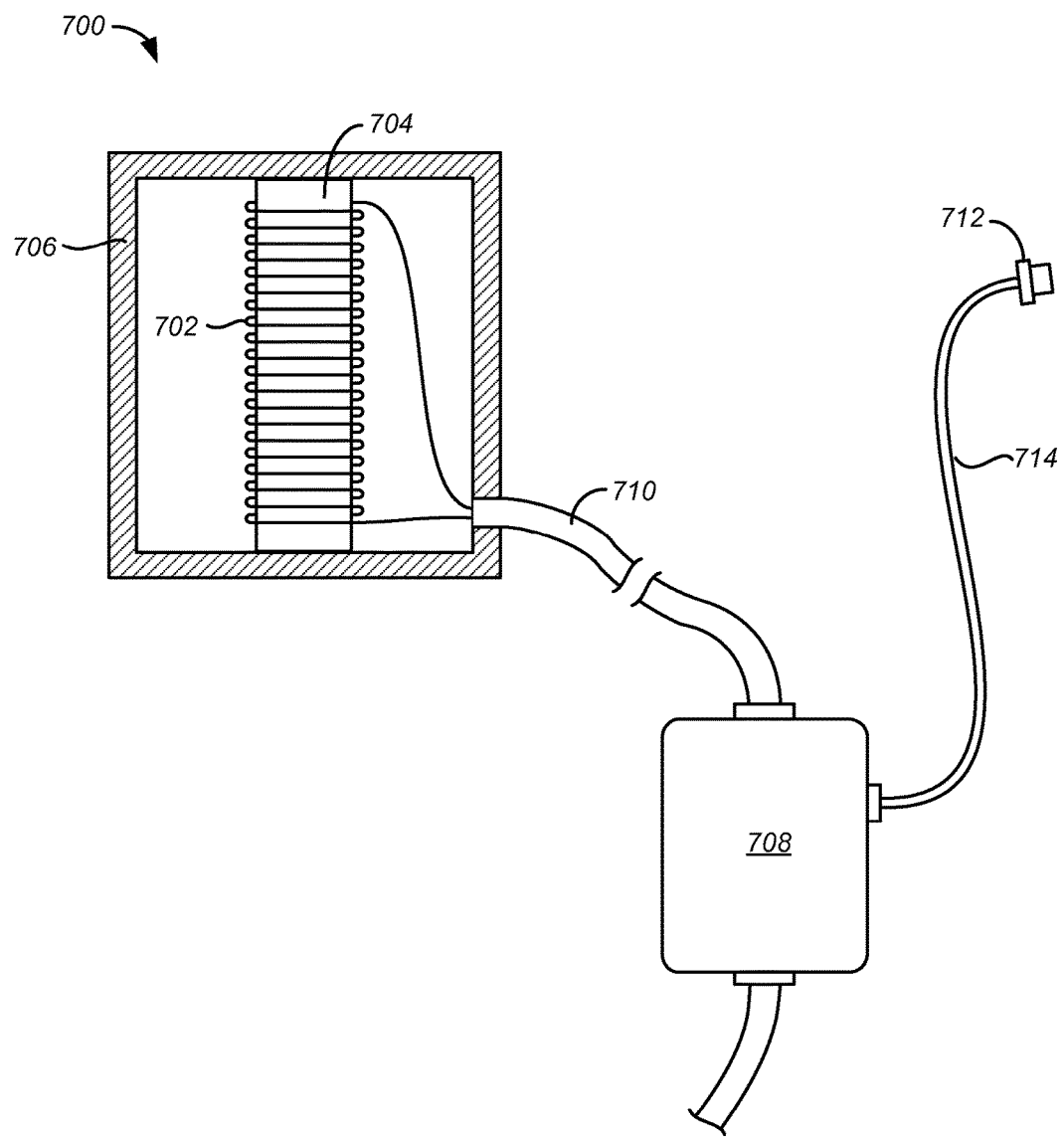
FIG. 10C illustrates an electromagnetic element useful in the magnetic element embodiments of the present invention.

In all embodiments described thus far, the magnetic element may comprise an electromagnet as illustrated in FIG. 10C. An electromagnetic element 700 may comprise a wire coil 702 wound over a coil 704 mounted within a housing 706. Current is typically provided by an external power supply 708 connected to the electromagnetic element by a conductor cable 710 or in some cases by a radiofrequency link. The power supply will include conventional circuitry to allow the magnetic field strength to be adjusted by the user, typically using a knob 712 or other convention manual controller connected to the power supply by a second cable 714. As described elsewhere herein, the ability to adjust the magnetic field strength of both the external magnet and the internal magnetic element affords a great deal of flexibility to the user.

Referring now to FIGS. 11A-11I, a method for magnetically suspending a tissue structure in a body cavity in accordance with the principles of the present invention will be described. The description will be made with respect to a tissue structure TS in an insufflated abdominal cavity A in a laparoscopic procedure, but the principles of the present invention will apply to other endoscopic and minimally invasive procedures and other body cavities as well. For ease of illustration, the presence of laparoscopic ports has not been shown, and in fact the tools of the present invention could be used without laparoscopic ports in some instances. Usually, however, the procedures would employ one or more conventional laparoscopic ports for providing tool access.

Figure 11A:
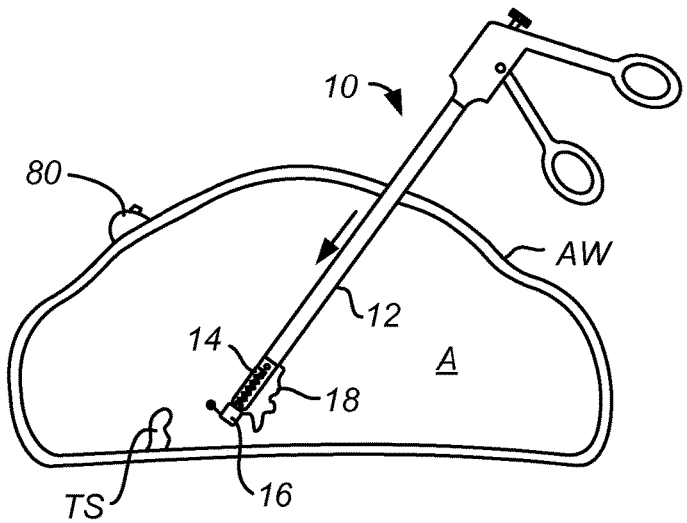
FIGS. 11A-11I illustrate the grasper placement tool of the present invention used for positioning a tissue grasper and magnetically suspending it in accordance with an exemplary embodiment of the methods of the present invention.

As shown in FIG. 11A, the grasper replacement tool 10 is introduced into the abdominal cavity A with the magnetic element 16 carried in the tissue grasper 14 which in turn is attached to the distal end of the shaft 12. By having these components axially aligned, the profile of the tool is minimized and the simultaneous introduction of all components is facilitated.

Figure 11B:
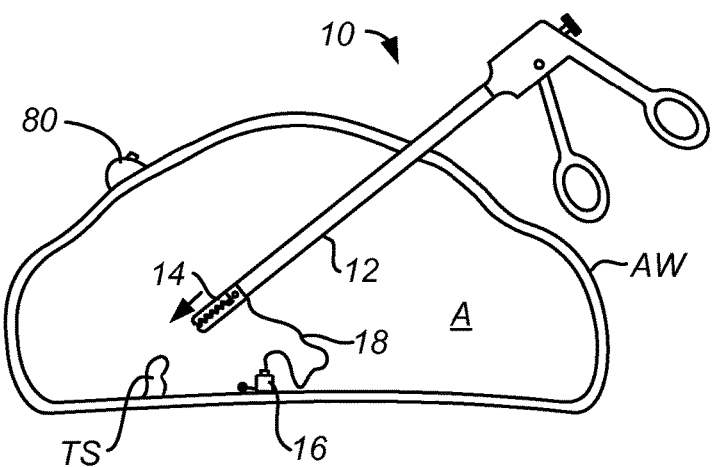
Figure 11C:
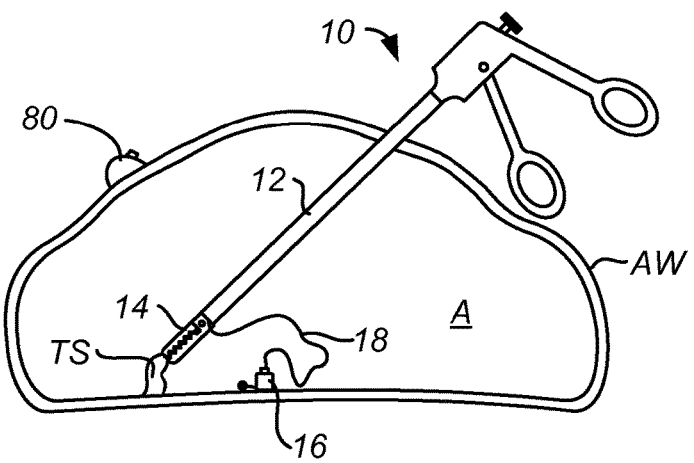

Once in the cavity, the jaws of the tissue grasper 14 (e.g. jaws 34 and 36 in FIG. 1) will be slightly opened to release the magnetic element 16, as shown in FIG. 11B. Any of the release mechanisms described above could be employed. The tissue grasper 14 is then moved to engage the tissue structure TS, and the jaws of the tissue grasper are tightened over the tissue structure, as shown in FIG. 11C, thus providing a firm grasp on the tissue structure.

Figure 11D:
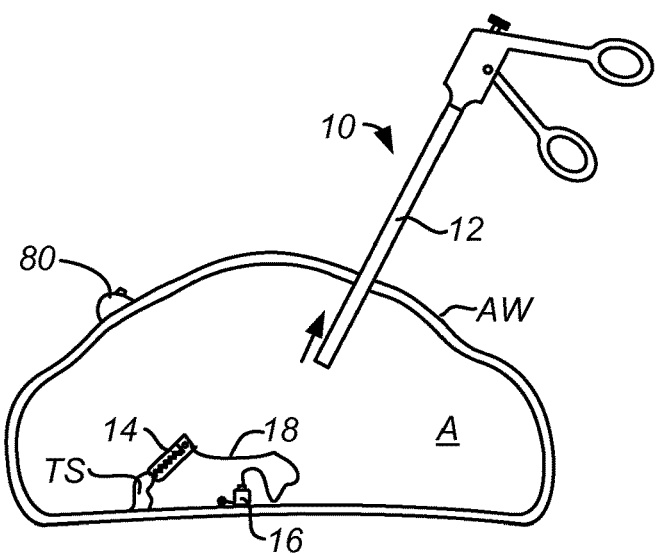

The tissue grasper 14 is then detached from the shaft 12 of the grasper placement tool 10, as shown in FIG. 11D. Any of the detachment mechanisms described above could be utilized. The grasper placement tool 10 is no longer used in this procedure for suspending the tissue structure, but it could be used for removing the tissue grasper 14 by performing the steps that are now being described in an opposite order.

Figure 11E:
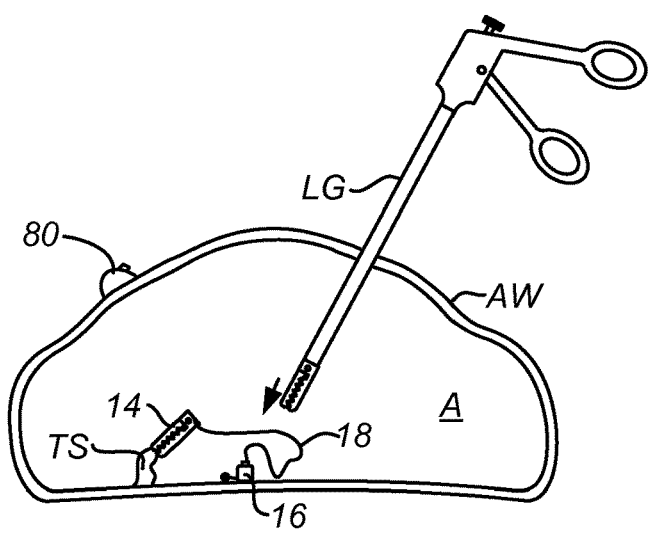
Figure 11F:
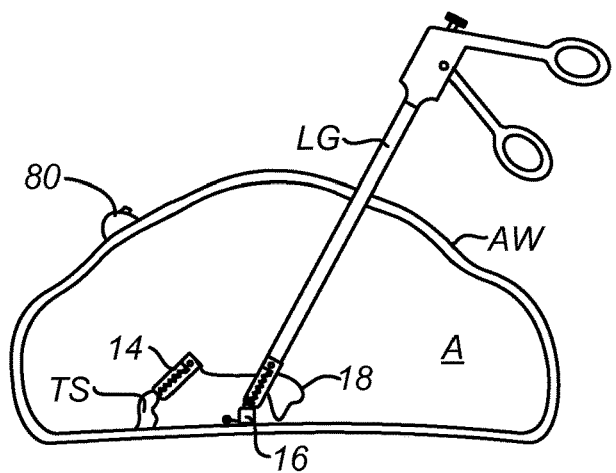
Figure 11G:
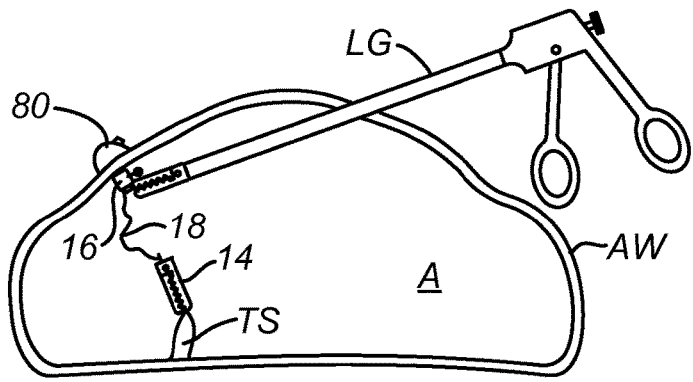
Figure 11H:
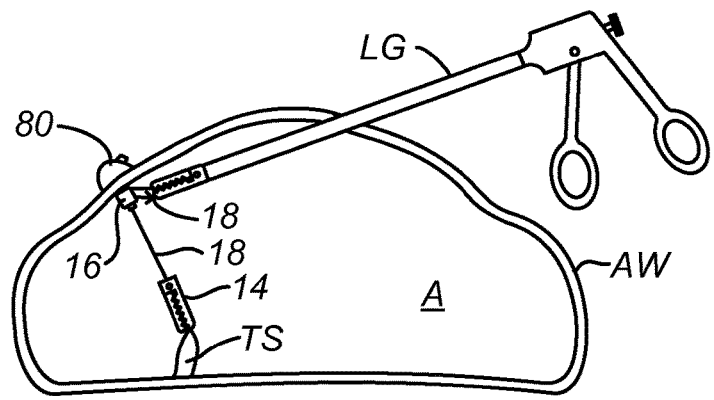
Figure 11I:
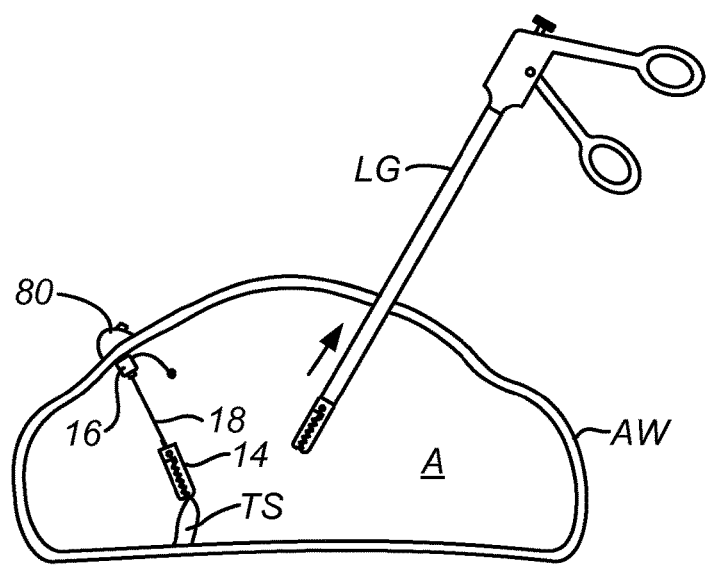

Referring now to FIG. 11E, a conventional laparoscopic grasper LG is next introduced into the abdominal cavity, optionally through the same port or tissue passage through which the grasper placement tool 10 has been passed. The jaws of the grasper LG are then used to grasp the magnetic coupling element 16, as shown in FIG. 11F. The magnetic coupling element 16 is next raised to the vicinity of an external magnet 80 which has been placed on the outer surface of the patient's abdominal wall AW, as shown in FIG. 11G. The strength of the magnetic field applied by the external magnet 80 may optionally be increased at this point in order to hold the coupling element 16 firmly as the tether 18 is cinched, as shown in FIG. 11H. The tether 18 may be cinched by using the jaws of grasper LG to grasp the free end of the tether and pull on said free end in order to tension the portion of tether 18 between the tissue grasper 14 and magnetic element 16, as shown in FIG. 11H. Once the proper tension has been applied, as shown in FIG. 11I, the grasper LG can be released from the magnetic coupling element 16, and the physician is ready to continue with other portions of the procedure.

An exemplary external magnet 80 is illustrated in FIGS. 12A and 12B. The external magnet 80 preferably includes a side coupler 82 which permits attachment to a support arm, as described hereinafter. An electromagnet is formed by wrapping a solenoid or coil wire 84 over a magnetic core 86 in a conventional manner. Magnetic field controller 88 is provided and connected to an electrical cord 90 to provide power. Both a field strength adjustment knob 92 and a lock button 94 may be provided for unlocking the support frame 180. An unlock button 96 may be provided for releasing the magnetic element 16. Of particular use, the magnetic field strength may be adjusted using the knob 92 to an appropriate level to facilitate movement of the external magnet 80 over the patient's skin in when it is desired to move the magnetic element 16 within the body cavity in order to manipulate the tissue structure TS. Circuits for smoothly adjusting the strength of an electromagnet from zero to maximum are well known in the art. See, for example, the circuit descriptions available at homemadecircuitsandschematics.blogspot.com.

Usually, the external magnet 80 will be held in place using a support frame 180, as shown in FIGS. 13A and 13B. The support frame 180 may include a stand 182 which may be secured to the side of a bed or table T. An arm 184, such as a shape lock mechanism, may be attached to an electronic lock 186 at the top of the stand 182. The electronic lock may be in communication with the lock and unlock buttons 94 and 96 on the external magnet 80, allowing the user to lock and unlock the arm while still holding the magnet. In this way, the external magnet 80 may be manually positioned over the patient P, and after the desired position is reached, the external magnet may be locked in place until it is desired to further move the magnet and the coupled tissue structure.

Figure 14A:
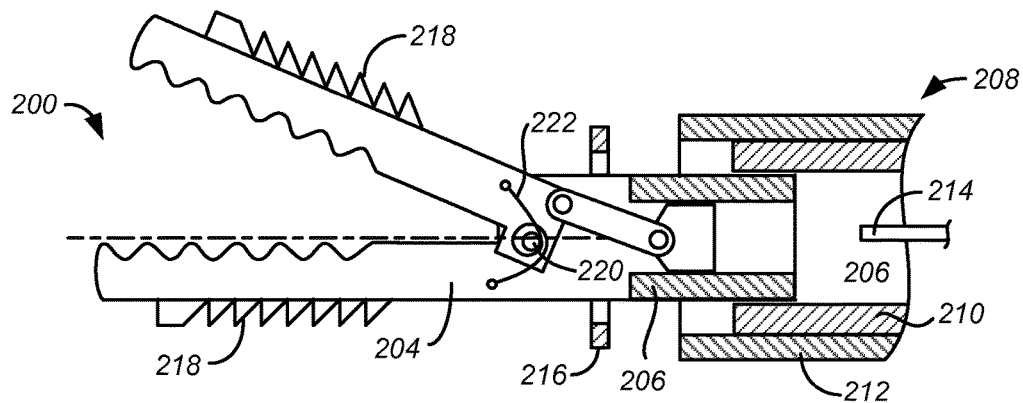
FIGS. 14A-14D illustrate a fourth exemplary embodiment of a tissue grasper constructed in accordance with the principles of the present invention.
Figure 14B:
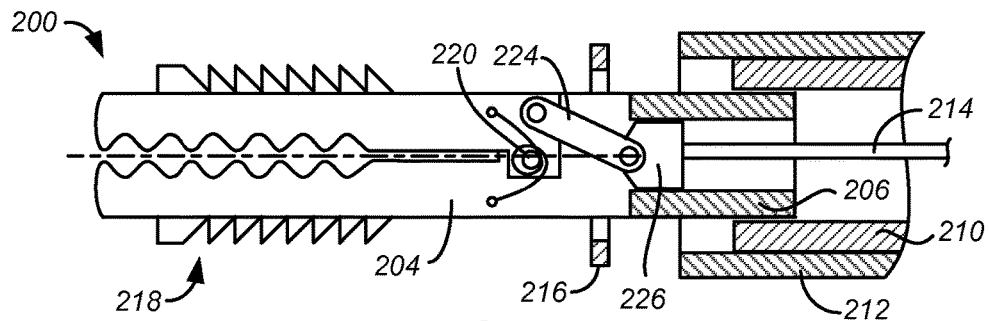

Referring now to FIGS. 14A-14D, a fourth exemplary tissue grasper 200 will be described. The tissue grasper 200 comprises an upper jaw 202 to pivotally attach to a lower jaw 204 and having a shank region 206 at a proximal end thereof. A grasper placement tool assembly 208 comprises an inner tubular member 210, an outer tubular member 212, and a reciprocating pusher 214. A retaining ring 216 is carried near a distal end of the outer tubular member and is adapted to be pushed forwardly over ratcheting surfaces 218 on the top and bottom of the upper jaw 202 and lower jaw 204, respectively. As shown in FIG. 14A, the upper jaw 202 and lower jaw 204 are held open by a spring 222 disposed about pivot member 220. The shank 206 is held within the open end of the inner tubular member 210, and pusher 214 may be advanced in a distal direction to engage a follower 226 attached to a link 224 which is configured to close the upper jaw 202 over the lower jaw 204, as shown in FIG. 14B.

Figure 14C:
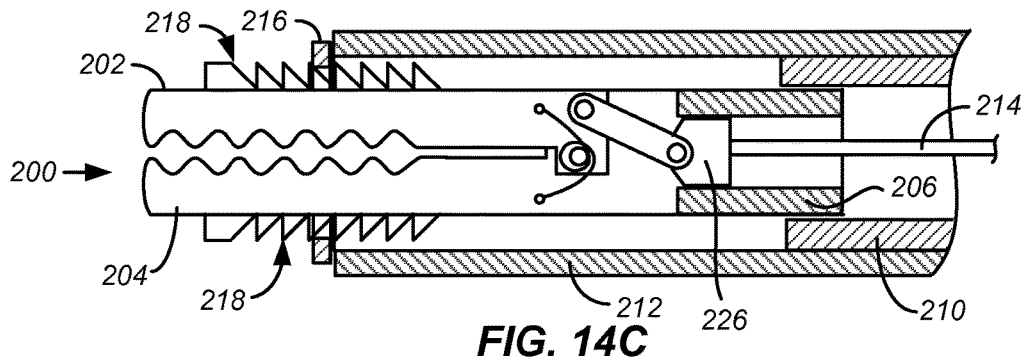
Figure 14D:
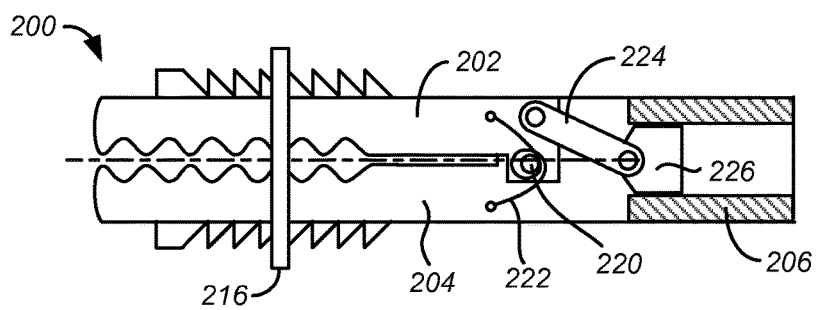

In order to hold the closed jaws together, the outer tubular member 212 may be advanced distally to push the retaining ring 216 over the ratcheting surfaces 218 of the upper and lower jaws, as shown in FIG. 14C. The jaws will be closed and the ratcheting ring 216 advanced after the tissue grasper 200 has been secured onto a desired tissue target site. The grasper placement tool assembly 208 may then be withdrawn from the closed tissue grasper 200, as shown in FIG. 14D.

Referring now to FIGS. 15A-15D, a fifth alternative exemplary tissue grasper 230 will be described. The tissue grasper 230 includes an upper jaw 232 pivotally attached to a lower jaw 234 and having a shank region 236 at its proximal end. A grasper placement tool 238 comprises a tubular body having a reciprocating pusher 240 mounted therein. The shank region 236 of the tissue grasper 230 is detachably received in an open end of the tubular body of the grasper placement tool 238. The upper jaw 232 is attached to scissor arm 244 and the lower jaw 234 is attached to a scissor arm 242. The scissor arms are mounted in an opening 246 formed in a distal region of the shank and attached by a pivot pin 248. The scissor arms 242 and 244 are configured so that advancement of the pusher 240 can open the jaws as will be described below.

Figure 15A:
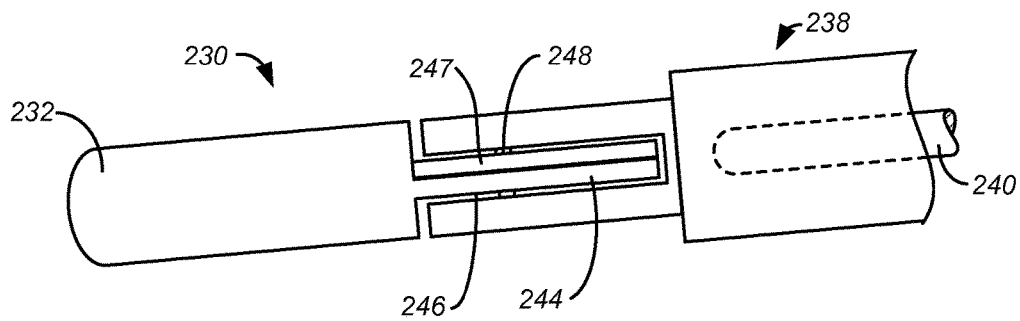
FIGS. 15A-15D illustrate a fifth exemplary embodiment of a tissue grasper constructed in accordance with the principles of the present invention.
Figure 15B:
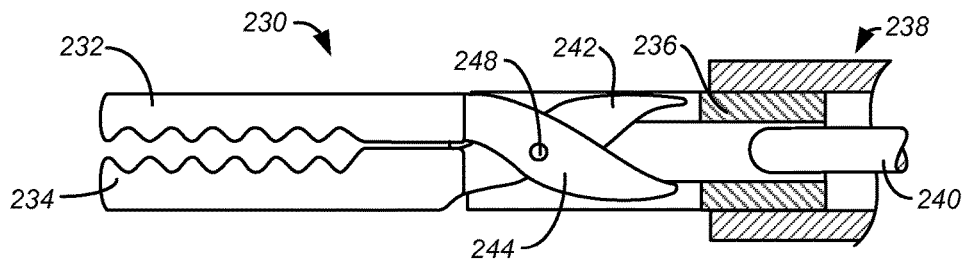
Figure 15C:
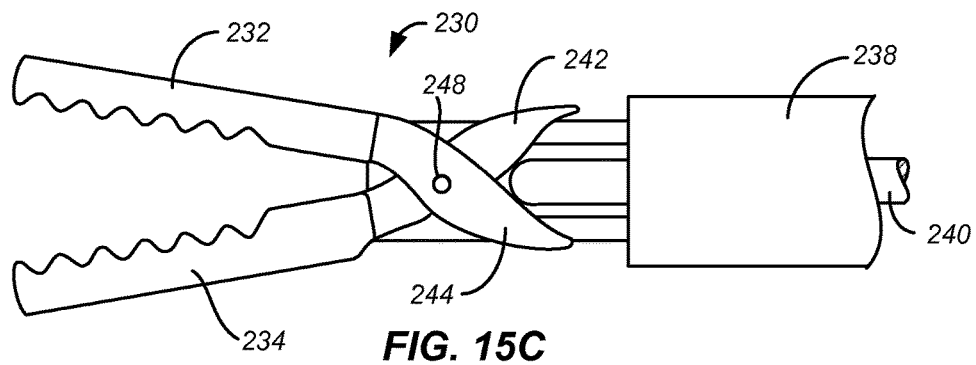
Figure 15D:
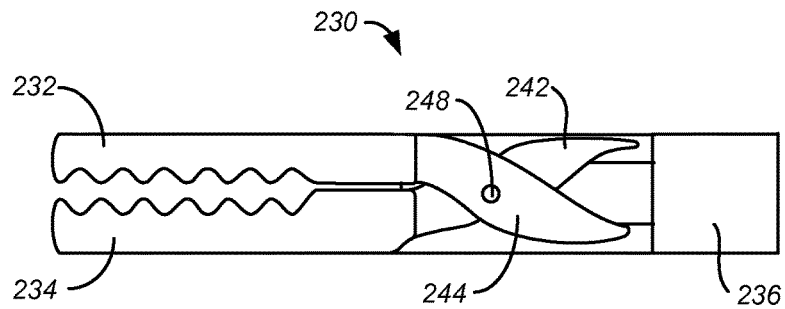

The upper jaw 232 and lower jaw 234 are normally held in their closed position, as shown in FIGS. 15A and 15B, by a spring element (not shown). In order to open the jaws, the pusher 40 is advanced to spread the interior ends of the scissor arms 242 and 244, as shown in FIG. 15C. So long as the pusher arm remains advanced, the jaws will remain open, allowing them to be placed over a tissue structure by proper manipulation of the grasper placement tool 238. When the target tissue is properly between the jaws, the pusher element 240 may be proximally retracted, allowing the spring element to close the jaws onto the tissue. Various further locking elements may be provided, such as a retaining ring as described previously.

Figure 16A:
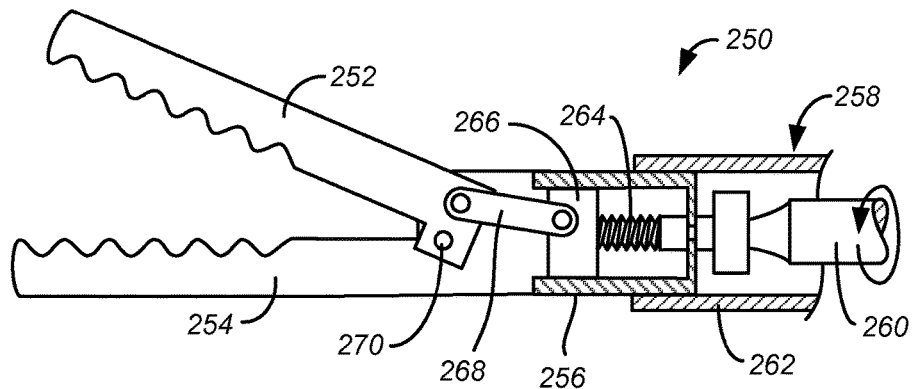
FIGS. 16A-16C illustrate a sixth exemplary embodiment of a tissue grasper constructed in accordance with the principles of the present invention.
Figure 16B:
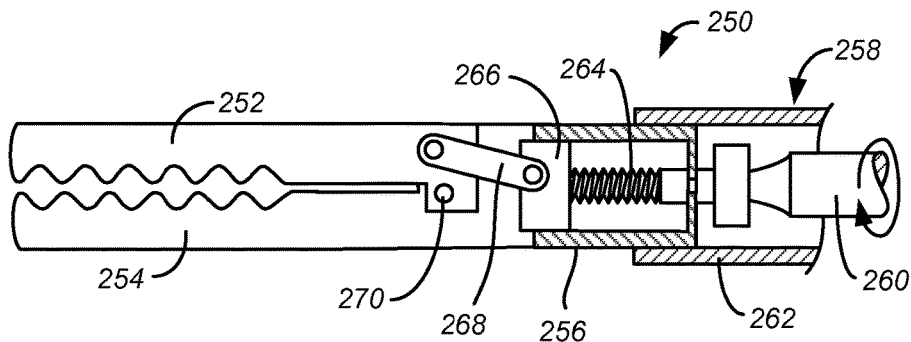
Figure 16C:
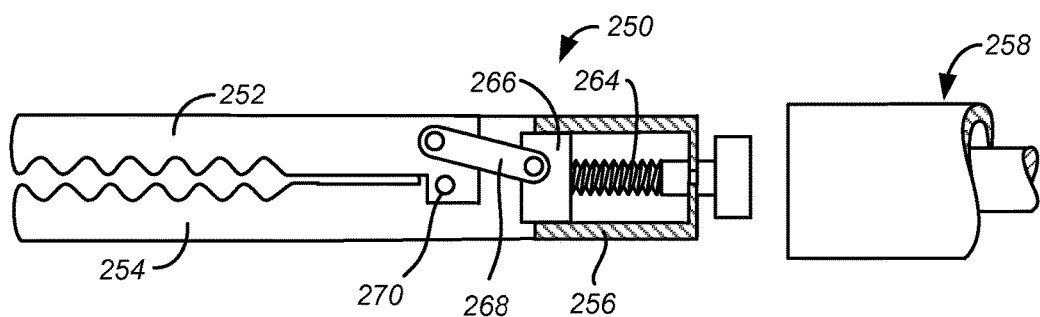

Referring now to FIGS. 16A-16C, a sixth exemplary tissue grasper 250 will be described. The tissue grasper 250 comprises an upper jaw 252 pivotally attached to a lower jaw 254 and having a shank region 256 at a proximal end thereof. The shank region 256 is carried in the open end of a grasper placement tool 258 having a tubular body. The grasper placement tool further includes a rotatable shaft 260 which is mounted within the tubular body 262. The rotatable shaft 260 is coupled to a threaded shaft 264, and a threaded follower rides over the threaded shaft so that rotation of the threaded shaft translates the follower proximally and distally. In its distal-most configuration, the follower 266 causes an attached link 268 to close the upper jaw which is mounted on pivot pin 270. By rotating the rotatable shaft 260 in the opposite direction, the threaded shaft draws the follower 266 in a proximal direction in order to open the upper jaw 252, as best seen in FIG. 16A. One advantage of the rotation drive mechanism is that no springs are required and the jaws 252 and 254 will be held in place by the friction of the threaded shaft 264 and follower 266. Another advantage of the rotation mechanism is that rotatable shaft 260 can be linked and rotated by a servo motor (not illustrated) which makes this mechanism ideal for use in robotic surgery. This provides for a very tight grasp of tissue. The grasper placement tool 258 may be removed from the tissue grasper 250 after the jaws have been closed over tissue, as shown in FIG. 16C. The jaws may then be removed by recoupling the grasper placement tool 258 in order to rotate the rotatable shaft 260 in the opposite direction in order to open the jaws and release them from the tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for manipulating an internal tissue structure using an external magnet, said method comprising:
   introducing a shaft through a percutaneous passage into a body cavity of a patient, wherein a distal end of the shaft carries a tissue grasper and a magnetic coupling element secured to the tissue grasper;
   securing the tissue grasper over the tissue structure while the tissue grasper remains on the shaft, wherein the shaft, tissue grasper, and the magnetic coupling element are aligned in tandem as they are introduced through the percutaneous passage;
   releasing the tissue grasper from the shaft after the grasper has been secured over the tissue structure, where the magnetic coupling element remains attached to the tissue grasper;
   positioning the external magnet over a patient's skin to create a magnetic field to attract and hold the magnetic coupling element;
   moving the external magnet over the patient's body surface in order to pull or drag the magnetic coupling element to position the tissue structure; and
   adjusting a strength of the magnetic field between the external magnet and the magnetic coupling element while moving the external magnet to facilitate movement of the external magnet over the patient's body surface to position the tissue structure.

2. A method as in claim 1, wherein the tissue grasper comprises opposed jaws and securing the tissue grasper over the tissue structure comprises closing the jaws over the tissue structure wherein the jaws remain closed after the tissue grasper is released from the shaft.

3. A method as in claim 2, wherein releasing the magnetic coupling element comprises opening the tissue grasper.

4. A method as in claim 1, wherein the adjusting the strength of the magnetic field between the external magnet and the magnetic coupling element comprises adjusting a magnetic strength of the external magnet.

5. A method as in claim 1, wherein the adjusting the strength of the magnetic field between the external magnet and the magnetic coupling element comprises adjusting a magnetic strength of the magnetic coupling element.

6. A method as in claim 1, wherein the adjusting the strength of the magnetic field between the external magnet and the magnetic coupling element comprises adjusting both a magnetic field of the external magnet and a magnetic field of the magnetic coupling element.

* * * * *